(12) United States Patent
Kwon et al.

(10) Patent No.: US 6,399,560 B1
(45) Date of Patent: Jun. 4, 2002

(54) BIOCIDE AND BIOCIDAL CLOTH CONTAINING A METAL PYRIDINETHIONE AND ADDITIONAL BIOCIDE

(75) Inventors: Hyo Sang Kwon; Steven Kritzler, both of Rosebery (AU)

(73) Assignee: Novapharm Research (Australia) Pty Ltd., Rosebery (AU)

(*) Notice: Subject to any disclaimer, the term of this patent is extended or adjusted under 35 U.S.C. 154(b) by 0 days.

(21) Appl. No.: 09/555,269

(22) PCT Filed: Nov. 26, 1998

(86) PCT No.: PCT/AU98/00984

§ 371 (c)(1),
(2), (4) Date: Aug. 4, 2000

(87) PCT Pub. No.: WO99/27792

PCT Pub. Date: Jun. 10, 1999

(30) Foreign Application Priority Data

Nov. 27, 1997 (AU) .............................................. PP0605

(51) Int. Cl.⁷ ................................................. C11D 3/48

(52) U.S. Cl. ...................... 510/382; 510/130; 510/131; 510/138; 510/386; 510/387; 510/388

(58) Field of Search ................................. 510/130, 131, 510/138, 382, 386, 387, 388

(56) References Cited

U.S. PATENT DOCUMENTS 4,581,351 A   4/1986   Berke et al. ................ 514/188

FOREIGN PATENT DOCUMENTS

| AU | 88238/91 | 5/1992 |
| JP | 53-118518 | 10/1978 |
| JP | 55-020753 | 2/1980 |

*Primary Examiner*—Charles Boyer
(74) *Attorney, Agent, or Firm*—Leydig, Voit & Mayer, Ltd.

(57) ABSTRACT

The invention provides a biocidal concentrate including zinc pyridinethione; and a second biocide selected to be biocidally effective in a pH range complementary to zinc pyridinethione. The second biocide may be an aromatic halogenated phenol such as triclosan, dichlorophen and trichlorcarban. The invention also provides biocidal cleaning devices and plastic materials and methods of manufacture thereof.

38 Claims, No Drawings

BIOCIDE AND BIOCIDAL CLOTH CONTAINING A METAL PYRIDINETHIONE AND ADDITIONAL BIOCIDE

TECHNICAL FIELD

This invention relates to a biocidal cleaning composition and the incorporation thereof into a biocidal cloth, sponge, paper, wound dressing, plastic or other substrate.

BACKGROUND ART

In domestic and hospital environments one of the most common methods of cleaning large surfaces is to wipe a cloth over such surfaces. Typically, the cloth will be moistened with water and may additionally have added a detergent or disinfectant. Cloths which do not contain a disinfectant are ineffective in controlling the growth of microorganisms. Indeed, the cloth itself may provide favourable conditions for the proliferation of such microorganisms and the action of wiping such an infected cloth over a surface may produce an effect counter to the desired outcome of making the surface more hygienic. Ordinary cleaning cloths which remain damp for a period are also notorious for the odours they develop, which are a result of microbial action.

Soaking a cloth in disinfectant provides fairly short term relief and requires the reapplication of the disinfectant to the cloth. While this method uses only modest amounts of disinfectant, the quantity is nevertheless much more than is required to achieve adequate bactericidal action. An extremely efficacious disinfectant is also required to prevent bacterial proliferation in the cleaning cloth itself, especially against the wide range of bacteria which are present in domestic and hospital situations. This somewhat unsophisticated method is also wasteful in that every time the cloth is rinsed or washed the disinfectant is removed and a new aliquot must be applied.

It has been practiced to incorporate an antimicrobial agen in a non-woven fabric as a colloidal suspension within an amorphous polymeric binder. The antimicrobial is not bound and is available to migrate to the surface of the binding agent. Such systems require an internal reservoir having a very large quantity of antimicrobial agent—typically 12 to 30 grams per square yard, and are more costly and less durable than is desired.

Cellulose sponges containing zinc pyridinethione as an active antibacterial agent are known. These sponges suffer from the drawback that a single wash in a washing machine is sufficient to remove much of the zinc pyridinethione. Thus, the sponge remains an effective weapon against bacteria for only a limited portion of its' working life, and may lead to users having false confidence in its' potency.

The reason that the zinc pyridinethione is so readily removed under normal washing conditions is that it is hydrolysed markedly at around pH 11. Zinc pyridinethione is an effective biocide, but suffers from the drawback that its optimal range of efficacy is within the pH range of 4.5 to 9.5. Many detergents and household cleaning agents have pH's above this range (for instance, washing powders give rise to solutions of around pH 11 and household bleaches have a pH of around 13), and, as in use they are often present in greater quantities than the zinc pyridinethione, are capable of rendering it ineffective.

The use of high concentrations of zinc pyridinethione to compensate for it's high loss under domestic cleaning conditions is undesirable as it has some human toxicity and is mildly irritating to the skin, and severely so to the eye. Further, the zinc pyridinethione has been shown to leach irreversibly out of the sponge over time.

There remains the problem then of providing a cleaning device, such as a cloth, sponge or similar, which will remain effective against a wide range of bacteria for a significant period of time, yet will not be unacceptably toxic.

Surprisingly, the inventor has found that one or more selected biocides, for example triclosan, dichlorophen (sometimes known as "dichlorophene" or DCP) or other chlorinated phenolic biocides, phenolic biocides, or trichlorocarban, in combination with an organometallic biocide, for example a metallic pyridinethione, exhibit a synergy which enables the combination to be effective against a wide range of bacteria under a wide range of pH conditions. Further, the addition of an acrylate binder, with or without other immobilising agents such as PVP, has also been found to render the biocidal mixture suitable for incorporation into a substrate for example a woven or non-woven cloth.

It is to be appreciated that such a biocide and method of binding is not limited to textiles used for cleaning, but may also be applicable to other materials, such as sponges, paper, wound dressings, plastics or even concrete.

DESCRIPTION OF THE INVENTION

It is to be understood that the use of the term "biocidal" throughout this specification is used in the sense that it refers to killing one or more organisms, and thus it embraces both the terms "biocidal" and "biostatic" as commonly referred to in relation to reducing or maintaining the number of microorganisms in a colony.

According to a first aspect the invention consists in a biocidal composition comprising a first biocide which is a metal pyridinethione; and a second biocide selected to be biocidally effective in a pH range complementary to the metal pyridinethione, said second biocide selected from the group consisting of halogenated phenols, phenols, derivatives of halogenated phenols, derivatives of phenols and trichlorcarban.

Examples of derivatives include diphenyl ether derivatives, methylene bridged derivatives and the like. The most preferred compounds are triclosan, dichlorophen and trichlorcarban. Examples of phenolic biocides which may be used include, but are not limited to, ortho-phenylphenol, methyl parahydroxybenzoate, propyl parahydroxybenzoate, ortho-cresol, meta-cresol and para-creso, said second biocide selected from the group consisting of halogenated phenols, phenols, derivatives of halogenated phenols, derivatives of phenols and trichlorcarban.

Examples of derivatives include diphenyl ether derivatives, methylene bridged derivatives and the like. The most preferred compounds are triclosan, dichlorophen and trichlorcarban. Examples of phenolic biocides which may be used include, but are not limited to, ortho-phenylphenol, methyl parahydroxybenzoate, propyl parahydroxybenzoate, ortho-cresol, meta-cresol and para-cresol.

Preferably the metal pyridinethione is zinc, sodium or magnesium pyridinethione, and most preferably it is zinc pyridinethione.

According to a second aspect the invention consists in a biocidal cleaning device comprising a biocidal composition according to the first aspect and a substrate.

According to a third aspect the invention consists in a method of making a biocidal cleaning device comprising the steps of combining a biocidal composition according to the first aspect with a binding agent and contacting the resultant formulation with a substrate. Preferably the method further includes the step of binding the composition to the substrate.

Preferably in a biocidal cleaning device the metal pyridinethione is present in amounts up to 2.5% of the weight of the device. More preferably it is present in amounts of 0.05 to 1.0% of the weight of the device. Most preferably it is present in amounts of 0.1 to 1.0% of the weight of the device.

Preferably in the biocidal cleaning device the second biocide is present in amounts up to 6% of the weight of the device. More preferably it is present in amounts of 0.05 to 2.0% of the weight of the device. Most preferably it is present in amounts of 0.1 to 2.0% of the weight of the device.

Desirably the biocidal composition is prepared as a concentrate which is diluted prior to impregnation into the substrate. In the concentrate the metal pyridinethione is present in amounts up to 40% w/w, and more preferably 20 to 30% w/w.

Preferably the second biocide is present in the biocidal concentrate in amounts up to 60% w/w, and more preferably 20 to 40% w/w.

The biocidal composition or concentrate may also include, in any combination, a mineral oil, (PVP) polyvinylpyrrolidone, an alcoholic solvent, an anionic surfactant, a non-ionic surfactant and water.

The substrate for use in the biocidal cleaning device is preferably cloth.

Preferably the cloth weight is from 30 to 200 $g/m^2$, and more preferably from 30–120 $g/m^2$ and the cloth is comprised of from: 70–100% rayon and 0–30% polyester. Preferably, the cloth also includes 0–30% polypropylene.

The substrate may also be sponge or a synthetic equivalent, paper or woven textile. In the case of a sponge, the weight can be up to 250 $g/m^2$ or more.

When binding the biocidal mixture onto a substrate, preferably the binding means comprises a heat activated crosslinking reaction. The heat activated crosslinking reaction may be carried out by a steam heated drum or by infra red means. The crosslinking reaction may also be activated by UV or visible light, electron beam or the like or chemical initiation.

The binding agent used in binding a biocidal mixture to a substrate may be a polymer latex formulation or acrylate, in particular acrylate copolymers.

When making a biocidal plastic material the plasticiser is optionally a hydrocarbon, preferably selected from the group comprising polybutene, low density polyethylene, low density polypropylene and paraffin wax. The plasticiser may also be, for example, an ester preferably selected from the group comprising dibutyl phthalate, dioctylphthalate, or epoxidised vegetable oil or blends thereof.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

BEST MODE FOR CARRYING OUT THE INVENTION

Preferred embodiments of the invention will now be described by way of example only. In the embodiments described zinc pyridinethione is used as the first biocide and triclosan as the second. However it will be understood that the invention is not limited to this embodiment.

The combination of zinc pyridinethione and triclosan or dichlorophen provides important advantages over the use of either disinfectant alone.

Zinc pyridinethione is effective at pH ranges from 4.5 to 9.5. As many detergents are strongly basic in nature, they can render zinc pyridinethione ineffective at very high pH's. Triclosan, dichlorophen, trichlorcarban, chlorinated phenolic biocides and phenolic biocides generally, on the other hand become more effective at higher pH ranges, in particular, at pH 9.5 and above.

In pH neutral or near neutral conditions, i.e. in the absence of large amounts of detergent, both the zinc pyridinethione and the complementary biocide work well. However, zinc pyridinethione, while effective against gram positive microorganisms, has been shown to be intrinsically only of limited effectiveness against gram negative bacteria. Triclosan and dichlorophen, for example, on the other hand while having some grain negative activity are particularly effective against gram positive bacteria. In particular, the combination of the zinc pyridinethione and the complementary biocide as described above, has been shown to exhibit a marked synergistic effect in killing Pseudomonas Aeruginosa.

The quantity of zinc pyridinethione used in the mixture to achieve a given bactericidal result is much less than if it was used alone, with the added advantage that less of this relatively toxic compound is used.

Thus, the combination of the two active ingredients is effective against a wide range of microorganisms at neutral pH's, and retains a good deal of this efficacy at higher pH's, in the presence of detergents.

The compositions of the present invention may also be used against mould.

Toxicologically, DCP is much safer than Zinc pyridinethione. Toxicological data is shown in table I. It is possible to formulate a biocidal mixture which has a high biocidal activity over a wide pH range, against a broad spectrum of microorganisms yet exhibiting with a low level of toxicity to humans.

TABLE I

| PROPERTY | DICHLOROPHEN | ZINC PYRIDINETHIONE |
|---|---|---|
| Melting Point ° C. | 175 | 240 |
| Decomp. ° C. | 290 | 240 |
| pH Stability | > activity > pH | decomposes pH > 9.5 |
| Oxidising Agents | incompatible | decomposes |
| Reducing Agents | no effect | decomposes |
| Biodegradability | Yes | No |
| Acute Toxicity | | |
| LD50 Oral | 3300 mg/kg | 160 mg/kg |
| LD50 Dermal | 5000 mg/kg | 100 mg/kg |
| LD50 Subcut | >3000 mg/kg | 730 mg/kg |
| LD 50 IV | 17 mg/kg | 10 mg/kg |
| Teratogenicity | no effect | reduced wt |
| Fish Toxicity | 23 mg/lt | not available |
| Irritancy | Slight dermal | Moderate dermal |
| | Moderate eye | Severe eye |
| Genotoxicity | None | None |
| Regulatory: | Max 0.1 mg/lt | Max 0.1 mg/lt |
| Pesticide | in waste water | in waste water |
| Heavy Metal | none | Max 10 mg/lt |

PVP (poly vinyl pyrrolidone) may be added optionally as a complexing material. PVP modifies the solubility and dispersibility of the biocide in water, as disclosed in PCT/AU96/00224.

The ability of PVP to modify the solubility and dispersibility have been found extremely useful when incorporating composite biocidal mixtures of the present invention onto a substrate, for example, cloth.

It is postulated that the PVP and the second (non-zinc pyridinethione) biocidal compound form a complex which provides excellent binding between the cloth and the active ingredients, retaining the biocidal dispersion and providing a longer effective life for the biocidal cloth. A postulated complex is shown in FIG. I. It will be appreciated that the dichlorophen need not be complexed with a single polymeric strand of the PVP, but may cross-link one or more other strands.

FIG. I. The structure of the complex formed between Dichlorophen and PVP

The most suitable fabrics for impregnation with the biocidal mixture are those which are rayon/polyester cloths which contain from 70 to 100 percent rayon, although most known fabrics perform adequately. In particular, fabrics which weigh between 30 and 200 $g/m^2$ and especially 30 and 120 $g/m^2$ have been found to be the most suitable.

Plasticisers are commonly added to synthetic polymers to modify their hardness and/or flexibility. Some common plasticisers are hydrocarbon polymers, such as polybutene, low density polyethylene, low density polypropylene and paraffin wax. Other commonly used plasticisers are esters, such as dibutyl phthalate, dioctyl phthalate and similar esters, such as epoxidised vegetable oils or blends thereof and similar esters.

The biocide combination can be dissolved into a plasticiser or plasticisers and then compounded into a polymer

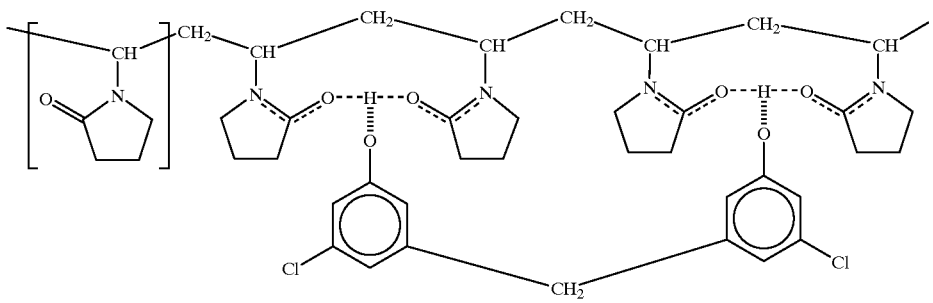

which is then moulded by extrusion, injection moulding or some other process. The resulting item would then resist the growth of microorganisms on the surface of the item by virtue of the incorporated biocides. If the plasticiser were selected so as to be incompatible with the bulk material, it leaches out slowly, carrying effective amounts of the biocidal composition with it to the surface.

A use of particular interest is on materials used in evaporative cooling systems. Such systems typically harbour a wide range of bacterial varieties, including legionella The use of a bound bactericide in such systems would provide a low but long lasting level of activity against bacteria. Such systems typically utilise a number of plastic plates, and impregnating these with a biocidal mixture and a binder which was incompatible with the plastic, so as to leach slowly to the surface, would provide a constantly self renewable biocidally active surface.

Preferably for disinfecting and cleaning, polyvinylpyrrolidones with a degree of polymerisation (K value) of 15, 30, 60 and 90, most preferably 90 or copolymers with vinylacetate comprising from 20 to 80% polyvinylpyrrolidone (most preferably comprising at least 50% vinylacetate and can possibly possess cationic character) are used.

For impregnation, the amount of PVP polymer used is preferably in the range of from 0.01 to 99.9 parts of the polymer for each part of biocide. More preferably the polymer is in the range of from 0.01 to 50 parts and most preferably 0.01 to 10 parts for each part of phenolic biocide.

The triclosan, DCP, trichlorocarban or other complementary biocide can at any time be substituted by a PVP/DCP, PVP/triclosan, PVP/trichlorocarban of PVP/complementary biocide combination.

The addition of a binding agent such as an acrylate enhances binding of the biocide into a woven or non-woven textile. The addition of polyvinylpyrrolidone has also been found to increase the binding of the biocidal agents to the cloth, either alone or in combination with the acrylate binder. More importantly, the addition of polyvinylpyrrolidone has been found to limit the biocide, so that as the surface wears, fresh biocide is exposed at the fresh surface.

The biocidal mixture in any of its forms can be mixed into binders such as acrylic or acrylic copolymer lattices or solutions, PVA lattices or PVA copolymer lattices or solutions, or any other polymer latex or solution or blend of any of the previously described polymers.

The biocidal mixture, with or without PVP or binding agents can be used for the treatment of any type of substrate, including woven or non-woven textile, fabrics, sponges, scourers and the like, paper, or any other material. The treatments can be applied from solutions, suspensions or emlulsions at ambient or other operational temperatures.

The inclusion of a mineral oil and an acrylate binder into the any of the above formulation can increase the suitability of the biocidal mixture for cloth impregnation.

EXAMPLES

The following formulation is prepared:

| Raw Material | % w/w |
|---|---|
| Example 1. Formulation of Biocidal Concentrate | |
| Zinc Pyridinethione | 17.19 |
| Dichlorophen | 34.39 |
| Mineral Oil | 22.92 |
| PVP | 8.44 |
| Ethanol | 3.44 |
| Sodium Lauryl Ether Sulfate | 0.70 |
| Dioctyl Sulfosuccinate | 1.50 |
| Water | qs 100% |

-continued

The following formulation is prepared:

| Raw Material | % w/w |
| --- | --- |
| *Example 2: Alternate Biocidal Concentrate* | |
| Zinc pyridinethione | 24.60 |
| Dichlorophen | 24.60 |
| Mineral Oil | 16.40 |
| PVP | 7.20 |
| Ethanol | 2.40 |
| Sodium Laurylether sulfate | 0.70 |
| Dioctyl Sulfosuccinate | 1.50 |
| Water | qs 100% |
| *Example 3. Binder Formulation* | |
| Acrylic polymer self crosslinking binder emulsion (approx 56% solids) | 46.0 |
| Defoamer emulsion (Foam Master, Henkel) | 0.15 |
| Acrylic copolymer viscosity controlling emulsion (Latekol DG, BASF) | 3.60 |
| Sodium dioctyl sulfosuccinate | 1.0 |
| Ammonium hydroxide (30%) | 1.0 |
| Ammonium nitrate | 1.0 |
| Dyestuff dispersion to standard colour | qs |
| Water | 47.25 |

The acrylic polymer binder emulsions is of a soft crosslinking type formulated with good tensile strength and rewetting properties for use in non-woven applications.

Example 4

Application to Fabric

In this process, bales of textile fibre are fed into a machine for making bonded, carded or hydroentangled non-woven fabric. These fibres can be of one type alone or of various combinations, for example most bonded, carded non wovens used for wipes are made from either rayon fibres or a combination of rayon and polyester fibres.

In the bonded, carded process the fibres are tangled together by one or more carding units in series, whereas the entangling takes place using high pressure water jets in hydroentangling. In both cases, at the end of the entangling stage the material is in continuous web form and is quite damp due to residual water which has been used in the course of each process.

The damp continuous web is then printed using a suitable dilution of the concentrate of example 1 or 2 and the binder of example 3, which is applied to isolated areas of the web. The damp, printed web passes through a heated zone to dry the printed fabric and cross-link the polymeric binder. These heated zones are usually either composed of steam heated drums over which the fabric passes and dries by contact, or else infra-red lamps which heat by radiation, or combinations of both.

This dry printed web is then rolled up for future slitting and cutting.

Example 5

Simulated Life Cycle of Cloth

The treated fabric is put into an automatic domestic clothes washing machine set on a warm wash (35° C.). Five cycles of washing were applied which constitutes the simulated useful life of the fabric. At the end of five cycles of washing the fabric is put through the following tests to validate that biocidal performance is still effective at the end of the working life of the fabric.

Example 6

Standard Sensory Tests

Standard sensory tests (stayfresh tests) were applied to the cloth to examine the resistance of the cloth to malodours produced by bacterial attack on food residues entrapped in the cloth in the normal course of kitchen use. Biocidal cloths produced according to the invention gave good results when subjected to the following tests:

AS2609.1, AS 2542.1.1, As 2542.1.2 and AS 2542.2.3

Example 7

Standard Quantitative Microbiological Test

A biocidal cloth according to the invention was subjected to a standard quantitative test for microorganisms, "Assessment of Antibacterial Finishes on Textile Materials": Test Method AATCC 100-1993. This test is specifically designed for the assessment of the biocidal properties of fabric treatments. These treatments are designed to kill microorganisms within the fabric, rather than on surfaces which come into contact with the fabric.

Example 8

Table II shows the effect of Pseudomonas Aeruginosa of fabric impregnated with zinc pyridinethione (0.85%), a second fabric impregnated with dichlorophen (0.85%) and a third fabric impregnated with a combination of dichlorophen (0.5%) and zinc pyridinethione (0.5%). The weights are given relative to the weight of dry fabric. A positive sign indicates an increase in the bacterial population and a negative sign shows a decrease.

TABLE II

| BIOCIDE | DAY 1 | DAY 2 |
| --- | --- | --- |
| zinc pyridinethione | +0.845 | +0.35 |
| dichlorophen | +0.439 | +2.12 |
| dichlorophen/zinc pyridinethione | −0.94 | −0.98 |

While the invention has been described herein with reference to zinc pyridinethione, those skilled in the art will appreciate that the use of other metal pyridinethiones also form part of the same inventive concept.

The claims of the present invention are as follows:

1. A biocidal concentrate comprising:
   a first biocide comprising 5–25% w/w of the concentrate, which is a metal pyridinethione; and
   a second biocide comprising 25–45% w/w of the concentrate which is selected to be biocidally effective in a pH range complementary to said metal pyridinethione, said second biocide selected from the group consisting of halogenated phenols, phenols, derivatives of halogenated phenols, derivatives of phenols and triclocarban.

2. The biocidal concentrate according to claim 1 wherein said metal pyridinethione is zinc pyridinethione.

3. The biocidal concentrate according to claim 1 wherein said metal pyridinethione is sodium pyridinethione.

4. The biocidal concentrate according to claim 1 wherein said metal pyridinethione is magnesium pyridinethione.

5. The biocidal concentrate according to claim 1 wherein the second biocide is dichlorophen.

6. The biocidal concentrate according to claim 1 wherein the second biocide is triclosan.

7. The biocidal concentrate according to claim 1 wherein the first biocide comprises 11–16% w/w of the concentrate.

8. The biocidal concentrate according to claim 1 wherein the second biocide comprises 32–37% w/w of the concentrate.

9. The biocidal concentrate according to claim 1 further including a mineral oil.

10. The biocidal concentrate according to claim 1 further including polyvinylpyrrolidone.

11. The biocidal concentrate according to claim 1 further including an alcoholic solvent.

12. The biocidal concentrate according to claim 1 further including water.

13. A biocidal cleaning device comprising
    a first biocide which is a metal pyridinethione;
    a second biocide which is selected to be biocidally effective in a pH range complementary to said metal pyridinethione, said second biocide selected from the group consisting of halogenated phenols, phenols, derivatives of halogenated phenols, derivatives of phenols, and triclocarban; and
    a substrate selected from cloth, sponge, synthetic equivalents of sponge, woven textile, non-woven textile, and paper,
wherein said biocides are in or on said substrate in a ratio of said first biocide to said second biocide of from 1:1 to 1:3.

14. The biocidal cleaning device according to claim 13 wherein the metal pyridinethione is present in an amount of up to 2.5% of the weight of the device.

15. The biocidal cleaning device according to claim 13 wherein the metal pyridinethione is present in an amount of 0.05–1.0% of the weight of the device.

16. The biocidal cleaning device according to claim 13 herein the metal pyridinethione is present in an amount of 0.1–1.0% of the weight of the device.

17. The biocidal cleaning device according to claim 13 wherein the second biocide is present in an amount up to 6% of the weight of the device.

18. The biocidal device according to claim 13 wherein the second biocide is present in an amount of 0.05–2.0% of the weight of the device.

19. The biocidal cleaning device according to claim 13 wherein the second biocide is present in an amount of 0.1–2.0% of the weight of the device.

20. The biocidal cleaning device according to claim 13 wherein the substrate is cloth.

21. The biocidal cleaning device according to claim 20 wherein the cloth weight is from 30–200 g/m².

22. The biocidal cleaning device according to claim 21 wherein the cloth weight is from 30–120 g/m².

23. The biocidal cleaning device according to claim 20 wherein the cloth is comprised of from:
    70–100% rayon; and
    0–30% polyester.

24. The biocidal cleaning device according to claim 23 comprising 0–30% polypropylene.

25. The biocidal cleaning device according to claim 13 wherein the substrate is sponge or a synthetic equivalent.

26. The biocidal cleaning device according to claim 13 wherein the substrate is paper.

27. The biocidal cleaning device according to claim 13 wherein the substrate is woven textile.

28. A method of making a biocidal cleaning device comprising the steps of:
    combining a biocidal concentrate comprising a first biocide which is a metal pyridinethione; and
    a second biocide which is selected to be biocidally effective in a pH range complementary to said metal pyridinethione, said second biocide selected from the group consisting of halogenated phenols, phenols, derivatives of halogenated phenols, derivatives of phenols, and triclocarban with a binding agent;
    contacting the resultant formulation with a substrate; and
    binding the formulation to the substrate with binding means.

29. The method according to claim 28 wherein said binding means is in the form of a heat treatment.

30. The method of making a biocidal cleaning device according to claim 29 wherein the heat treatment is carried out by a steam heated drum.

31. The method of making a biocidal cleaning device according to claim 29 wherein the heat treatment is applied by infra red means.

32. The method according to claim 28 wherein said binding means is in the form of UV or visible light.

33. The method of making a biocidal cleaning device according to claim 28 wherein the binding agent is a polymer latex formulation.

34. The method of making a biocidal cleaning device according to claim 28 wherein the binding agent is acrylate.

35. The method of making a biocidal cleaning device according to claim 28 wherein the substrate is selected from the group comprising cloth, sponge or a synthetic equivalent, paper and woven textiles.

36. The method of making a biocidal cleaning device according to claim 28 wherein the substrate is cloth.

37. The cleaning device of claim 13, wherein said first biocide and said second biocide are contained in a binding agent which is bound to said substrate, and said cleaning device is washable and reusable.

38. The cleaning device of claim 13, further comprising a binder containing said first biocide and said second biocide and bound to said substrate.

* * * * *